US009174848B2

(12) United States Patent  
Zou et al.

(10) Patent No.: US 9,174,848 B2  
(45) Date of Patent: Nov. 3, 2015

(54) PROCESSES AND SYSTEMS FOR PURIFYING SILANE

(71) Applicant: SunEdison, Inc., Maryland Heights, MO (US)

(72) Inventors: Baisheng Zou, Pearland, TX (US); Zhihui Gu, Houston, TX (US)

(73) Assignee: SunEdison, Inc., Maryland Heights, MO (US)

( * ) Notice: Subject to any disclaimer, the term of this patent is extended or adjusted under 35 U.S.C. 154(b) by 0 days.

(21) Appl. No.: 14/549,145

(22) Filed: Nov. 20, 2014

(65) Prior Publication Data

US 2015/0075969 A1 Mar. 19, 2015

Related U.S. Application Data

(62) Division of application No. 13/709,318, filed on Dec. 10, 2012, now Pat. No. 9,061,916.

(60) Provisional application No. 61/581,728, filed on Dec. 30, 2011.

(51) Int. Cl.  
*B01D 3/34* (2006.01)  
*C01B 33/04* (2006.01)  
*F25J 3/02* (2006.01)  
*B01D 3/00* (2006.01)  
*B01D 3/14* (2006.01)  
*C07F 7/08* (2006.01)  
*B01D 3/36* (2006.01)  
*B01J 19/24* (2006.01)

(52) U.S. Cl.  
CPC .............. *C01B 33/046* (2013.01); *B01D 3/009* (2013.01); *B01D 3/143* (2013.01); *B01D 3/36* (2013.01); *B01J 19/24* (2013.01); *C07F 7/0896* (2013.01); *F25J 3/0209* (2013.01); *B01J 2219/24* (2013.01)

(58) Field of Classification Search  
USPC .......................................... 423/346, 347, 349  
See application file for complete search history.

(56) References Cited

U.S. PATENT DOCUMENTS

| 3,886,221 A | 5/1975 | Agee et al. |
| 3,903,183 A | 9/1975 | Wikman et al. |
| 4,099,936 A | 7/1978 | Tarancon |
| 4,340,574 A | 7/1982 | Coleman |
| 4,554,141 A | 11/1985 | Scull et al. |
| 4,610,858 A | 9/1986 | Yamada et al. |
| 4,632,816 A | 12/1986 | Marlett |
| 4,676,967 A | 6/1987 | Breneman |
| 5,075,092 A | 12/1991 | Boone et al. |
| 5,206,004 A | 4/1993 | Park |
| 5,211,931 A | 5/1993 | Allen et al. |
| 5,681,908 A | 10/1997 | Mehra et al. |
| 5,735,141 A | 4/1998 | Whitlock |
| 6,399,812 B1 | 6/2002 | Yan et al. |
| 6,942,844 B2 | 9/2005 | Muller et al. |
| 8,524,048 B2 | 9/2013 | Gu et al. |
| 8,551,298 B2 * | 10/2013 | Truong et al. .................. 203/81 |
| 2011/0201846 A1 | 8/2011 | Fujiwara et al. |

FOREIGN PATENT DOCUMENTS

| EP | 0811815 A2 | 10/1997 |
| KR | 20030052379 A | 6/2003 |
| WO | 2011055057 A1 | 5/2011 |

OTHER PUBLICATIONS

Müller et al.: Development and Economic Evaluation of a Reactive Distillation Process for Silane Production, Distillation and Adsorption: Integrated Processes, 2002, Bayer AG, D-51368 Leverkusen, http://www.nt.ntnu.no/users/skoge/prost/proceedings/distillation02/dokument/4-1.pdf, 11 pages.  
Co-Owned U.S. Appl. No. 12/898,494, filed Oct. 5, 2010, pp. 36.  
Co-owned U.S. Appl. No. 13/246,571, filed Sep. 27, 2011, pp. 38.  
Co-owned U.S. Appl. No. 13/246,574, filed Sep. 27, 2011, pp. 36.  
Co-owned U.S. Appl. No. 12/898,487 entitled filed on Oct. 5, 2010, pp. 33.  
Non-Final Office Action, U.S. Appl. No. 12/898,494, dated Dec. 19, 2012, pp. 12.  
Non-Final Office Action, U.S. Appl. No. 13/246,571, dated Jan. 3, 2013, pp. 29.  
Non-Final Office Action, U.S. Appl. No. 12/898,487, dated Dec. 18, 2012, pp. 14.  
Non-Final Office Action, U.S. Appl. No. 13/246,574, dated Jan. 11, 2013, pp. 19.  
International Search Authority—Invitation to Pay Additional Fees and, Where Applicable, Protest Fee, Application No. PCT/US2011/052588, dated Jan. 6, 2012, pp. 7.  
Couper, James R.; Penney, W. Roy; Fair, James R.; Walas, Stanley M. Sep. 8, 2009, Chemical Process Equipment-Selection and Design, 3rd Edition, pp. 126-135.  
Douglas, A.P.; Hoadley, A.F.A.; A process integration approach to the design of two- and three-column methanol distillation schemes, Aug. 24, 2005, Applied Thermal Engineering, vol. 26, pp. 338-349.  
Coker, A. Kayode, Ludwig's Applied Process Design for Chemical and Petrochemical Plants, Jun. 10, 2010, Gulf Professional Publishing, vol. 2, 4th Edition, pp. 257-260.  
International Search Report and Written Opinion, Application No. PCT/US2012/068362, dated Jun. 4, 2013, pp. 14.  
Non-Final Office Action, U.S. Appl. No. 13/709,318, dated Dec. 16, 2014, pp. 8.

\* cited by examiner

*Primary Examiner* — Sudhakar Katakam  
*Assistant Examiner* — Pancham Bakshi  
(74) *Attorney, Agent, or Firm* — Armstrong Teasdale LLP

(57) ABSTRACT

Processes and systems for purifying silane-containing streams and, in particular, for purifying silane-containing streams that also contain ethylene are disclosed. The processes and systems may be arranged such that one or more ethylene reactors are downstream of light-end distillation operations.

10 Claims, 3 Drawing Sheets

PROCESSES AND SYSTEMS FOR PURIFYING SILANE

CROSS-REFERENCE TO RELATED APPLICATIONS

This application is a divisional of U.S. patent application Ser. No. 13/709,318, filed Dec. 10, 2012, which claims the benefit of U.S. Provisional Application No. 61/581,728, filed Dec. 30, 2011, both of which are incorporated herein by reference it their entirety.

FIELD OF THE DISCLOSURE

The field of the disclosure relates to purification of silane-containing streams and, particularly, to methods for purifying silane that are relatively simple in design and operation and which may operate with less heating and cooling of process streams. The disclosure also relates to systems for carrying out such purification operations.

BACKGROUND

Silane is a versatile compound that has many industrial uses. In the semiconductor industry, silane may be utilized for deposition of an epitaxial silicon layer on semiconductor wafers and for production of polycrystalline silicon. Polycrystalline silicon is a vital raw material used to produce many commercial products including, for example, integrated circuits and photovoltaic (i.e., solar) cells that may be produced by thermal decomposition of silane onto silicon particles in a fluidized bed reactor.

Silane may be produced by reacting silicon tetrafluoride with an alkali or alkaline earth metal aluminum hydride such as sodium aluminum tetrahydride as disclosed in U.S. Pat. No. 4,632,816, which is incorporated herein by reference for all relevant and consistent purposes. Silane may alternatively be produced by the so-called "Union Carbide Process" in which metallurgical-grade silicon is reacted with hydrogen and silicon tetrachloride to produce trichlorosilane as described by Müller et al. in "Development and Economic Evaluation of a Reactive Distillation Process for Silane Production," *Distillation and Adsorption: Integrated Processes*, 2002, which is incorporated herein by reference for all relevant and consistent purposes. The trichlorosilane is subsequently taken through a series of disproportionation and distillation steps to produce a silane end-product.

After silane is produced, it is conventionally taken through a purification process to remove impurities prior to use (e.g., prior to epitaxial layer production or polycrystalline silicon production). Examples of impurities that may be present in the silane-containing process streams include, for example, nitrogen, methane, hydrogen, ethane, ethylene, ethylsilane, diethylsilane, toluene, dimethoxyethane and combinations of these impurities.

A continuing need exists for processes for purifying silane-containing process streams and, in particular, processes that are relatively less complex than conventional processes and that achieve relatively high silane purity and a relatively high rate of silane recovery. A need also exists for systems for carrying out such processes.

This section is intended to introduce the reader to various aspects of art that may be related to various aspects of the disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

One aspect of the present disclosure is directed to a process for purifying a silane-containing stream that contains silane, ethylene and one or more compounds having a boiling point less than silane. The silane-containing stream is introduced into a reactor to convert ethylene to at least one of ethylsilane and ethane and to produce an ethylene-depleted stream relative to the silane-containing stream. The ethylene-depleted stream is introduced into a light-ends distillation column to produce a silane-depleted overhead fraction and a silane-enriched bottoms fraction relative to the ethylene-depleted stream. The silane-enriched bottoms fraction contains silane and at least one of ethylsilane and ethane.

Another aspect of the present disclosure is directed to a system for purifying a silane-containing stream that contains silane, ethylene and one or more compounds having a boiling point less than silane. The system includes a reactor for converting ethylene to at least one of ethylsilane and ethane and for producing an ethylene-depleted stream relative to the silane-containing stream. The system includes a light-ends distillation column for producing a silane-depleted overhead fraction and a silane-enriched bottoms fraction relative to the ethylene-depleted stream, the silane-enriched bottoms fraction containing silane and at least one of ethylsilane and ethane. The system also includes a conveying apparatus for conveying the ethylene-depleted stream from the reactor to the light-ends distillation column.

A further aspect of the present disclosure is directed to a process for purifying a silane-containing stream that contains silane, ethylene and one or more compounds with a boiling point less than silane. The silane-containing stream is introduced into a reactor to convert ethylene to at least one of ethylsilane and ethane and to produce an ethylene-depleted stream relative to the silane-containing stream. The ethylene-depleted stream is introduced into a heavy-ends distillation column to produce a silane-enriched overhead fraction and a silane-depleted bottoms fraction relative to the ethylene-depleted stream. The silane-depleted bottoms fraction is enriched in at least one of ethylsilane and ethane relative to the ethylene-depleted stream. The overhead fraction produced from the heavy-ends distillation column is introduced into a light-ends distillation column to produce a silane-depleted overhead fraction and a silane-enriched bottoms fraction relative to the overhead fraction produced from the heavy-ends distillation column. The silane-depleted overhead fraction is enriched in compounds with a boiling point less than silane relative to the overhead fraction produced from the heavy-ends distillation column.

Yet another aspect of the present disclosure is directed to a system for purifying a silane-containing stream that includes silane, ethylene and one or more compounds having a boiling point less than silane. The system includes a reactor for converting ethylene to at least one of ethylsilane and ethane and for producing an ethylene-depleted stream relative to the silane-containing stream. The system also includes a heavy-ends distillation column for producing a silane-enriched overhead fraction and a silane-depleted bottoms fraction relative to the ethylene-depleted stream, the silane-depleted bottoms fraction being enriched in at least one of ethylsilane and ethane. The system includes a conveying apparatus for conveying the ethylene-depleted stream from the reactor to the heavy-ends distillation column. The system also includes a light-ends distillation column for producing a silane-depleted overhead fraction and a silane-enriched bottoms fraction relative to the overhead fraction produced from the heavy-ends distillation column, the silane-depleted overhead fraction being enriched in compounds with a boiling point less than silane relative to the overhead fraction produced from the heavy-ends distillation column. The system includes a conveying apparatus for conveying the overhead fraction produced from the heavy-ends distillation column to the light-ends distillation column.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

In accordance with various embodiments of the present disclosure, processes for purifying silane that involve reacting ethylene to produce at least one of ethylsilane and ethane prior to removal of light-end impurities are herein disclosed. Further, purification systems for carrying out such processes are provided. By reacting ethylene prior to light-ends separation, the amount of energy which is transferred into and/or out of streams entering and exiting the reactor may be reduced.

Processes for Purifying Silane

Figure 1:
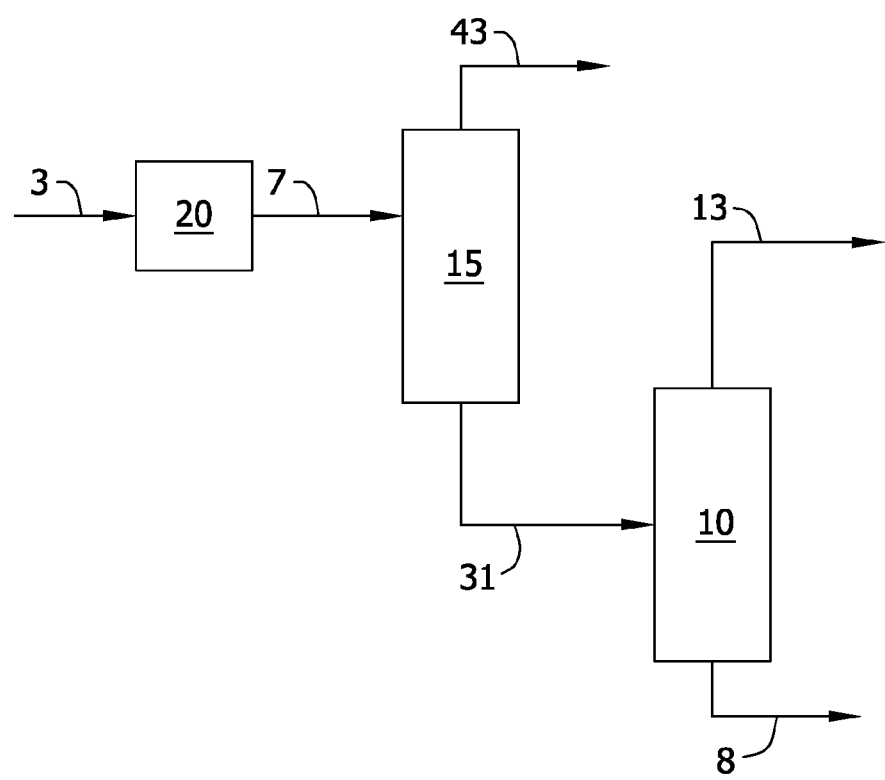
FIG. 1 is a schematic of a system for purifying silane from a silane-containing stream that contains ethylene.

Referring now to FIG. 1 in which a process for purifying silane is shown schematically in accordance with embodiments of the present disclosure, a silane-containing stream 3 is subjected to various downstream purification operations. Silane-containing streams that may be purified according to embodiments of the present disclosure may contain a wide variety of impurities and may contain those impurities in a wide range of amounts without departing from the scope of the present disclosure. The silane-containing stream 3 may have been subjected to one or more purification steps prior to performing the purification process of embodiments of the present disclosure (e.g., removal of an amount of impurities with a boiling point less than silane or a boiling point greater than silane). The amount of silane in the silane-containing stream prior to being subjected to the purification processes of the present disclosure may be at least about 10 wt %, at least about 30 wt %, at least about 50 wt %, at least about 70 wt %, at least about 85 wt %, at least about 95 wt % or even at least about 99 wt % (e.g., from about 50 wt % to about 99 wt % or from about 70 wt % to about 99.9 wt %).

The silane-containing stream 3 may be substantially free (e.g., contain less than about 0.1 mol % or less than about 0.01 mol %) of alkali or alkaline earth-metal silanes and, alternatively or in addition, may be substantially free of trichlorosilane, tetrachlorosilane and tetrafluorosilane. In some embodiments, these compounds are substantially removed from the silane-containing stream prior to performing the processes of the present disclosure.

The silane-containing stream 3 that is subjected to the processes of the present disclosure may contain one or more impurities with a boiling point less than silane and/or one or more impurities with a boiling point greater than silane. In this regard, the boiling point of silane is about −112° C. Impurities that have a boiling point greater than silane include, for example, ethane, ethylene, ethylsilane, diethyl silane, toluene, and dimethoxyethane. Impurities that have a boiling point less than silane include, for example, hydrogen, nitrogen, and methane. The silane-containing stream 3 typically will contain ethylsilane. In various embodiments, the silane-containing stream contains at least about 1 ppm ethylene by weight, or at least 50 ppm, at least about 100 ppm, at least about 250 ppm, at least about 500 ppm, at least about 750 ppm ethylene by weight (from about 1 ppm to about 2000 ppm, from about 1 ppm to about 1000 ppm or from about 100 ppm to about 1000 ppm ethylene by weight).

The starting silane-containing stream 3 may be a gas or may be a liquid without departing from the scope of the present disclosure. In this regard, the silane-containing stream may be within any range of temperatures and pressures including, but not limited to, pressure and temperatures typical of silane production and/or processing.

The silane-containing stream 3 is introduced into a reactor 20 to convert ethylene that is present in the silane-containing stream to at least one of ethylsilane and ethane. The reactor 20 may include one or more catalysts therein which promote conversion of ethylene. Any catalyst available to those of skill in the art which promotes reaction of ethylene may be used. Suitable catalysts include zeolite catalysts such as those disclosed in U.S. Pat. Nos. 4,554,141; 5,206,004 and 5,211,931, each of which is incorporated herein by reference for all relevant and consistent purposes. In some embodiments the catalyst is a zeolite-supported platinum, palladium or nickel catalyst. The catalyst (e.g., zeolite) may form part of a fixed bed and/or may form a molecular sieve.

Ethylene in the silane-containing stream 3 may be converted to ethylsilane by reaction (1) shown below $$C_2H_4 + SiH_4 \rightarrow C_2H_5SiH_3 \quad (1).$$

Alternatively or in addition, ethylene may be converted to ethane in the reactor 20 according to reaction (2) shown below:

$$C_2H_4 + H_2 \rightarrow C_2H_6 \quad (2).$$

It should be noted that while reactions (1) and (2) may be the principal reactions that occur in the reactor, they do not represent all reactions that may take place in the reactor and other compounds may be produced without limitation. In some embodiments of the present disclosure, at least about 75% of the ethylene is converted to ethylsilane or ethane or at least about 85% or at least about 90% of ethylene is converted to ethylsilane or ethane (e.g., from about 75% to about 95% or from about 85% to about 95% ethylene is converted to ethylsilane or ethane).

The silane-containing stream 3 may be compressed (i.e., pressurized) prior to introduction into the reactor 20. In some embodiments, the silane-containing stream 3 is compressed to a pressure of at least about 2000 kPa (atmospheric) or at least about 2100 kPa, at least about 2200 kPa or at least about 2300 kPa (e.g., from about 2100 kPa to about 2350 kPa).

Generally the silane-containing stream 3 need not be condensed into a liquid; however, such condensation operations are within the scope of the present disclosure. In some embodiments, the temperature of the silane-containing stream 3 is at least about 25° C. prior to entry into the reactor 20 to promote conversion of ethylene to ethylsilane or ethane or at least about 100° C., at least about 150° C. or from about 25° C. to about 230° C., from about 100° C. to about 230° C. or from about 150° C. to about 230° C. prior to entry into the reactor 20. In some embodiments, the silane-containing stream 3 is heated by use of a heater (not shown). Suitable heaters include heat exchangers that exchange heat with another stream (e.g., interchangers), indirect combustion burners and electric heaters.

Upon exiting the reactor 20, the ethylene-depleted stream 7 may be condensed into a liquid in a condenser (not shown) and introduced into a light-ends distillation column 15 to produce a silane-enriched bottoms fraction 31 and silane-depleted overhead fraction 43 relative to the ethylene-depleted stream 7. As used herein, "light-ends distillation column" refers to a distillation column in which at least about 50 wt % of the compounds with a boiling point less than silane are separated from the light-ends distillation column feed stream (or feed streams when more than one feed stream is used). Generally, these separated compounds are removed from the distillation column 15 in the silane-depleted overhead fraction 43. In some embodiments of the present disclosure, the overhead fraction 43 contains at least about 50 wt % of the compounds with a boiling point less than silane in the silane-containing stream 3 and, in other embodiments, at least about 60 wt %, at least about 75 wt %, at least about 90 wt % or even at least about 95 wt % of the compounds with a boiling point less than silane in the silane-containing stream 3. The silane-depleted overhead fraction 43 may contain amounts of silane such as at least about 40 wt % silane and, in other embodiments, at least about 50 wt %, at least about 60 wt %, at least about 70 wt % or at least about 75 wt % silane.

Generally, the overhead fraction 43 is enriched in compounds with a boiling point less than silane and depleted in compounds with a boiling point greater than silane. The silane-enriched bottoms fraction 31 includes silane and is enriched in compounds with a boiling point greater than silane such as ethylsilane and/or ethane produced in reactor 20.

The ethylene-depleted stream 7 may be cooled prior to entry into the light-ends distillation column 15 such as to a temperature less than about 35° C., less than about 25° C., less than about 0° C. or less than about −25° C. (e.g., from about 35° C. to about −30° C. or from about 20° C. to about −20° C.). Any suitable type of cooler or series of cooling operations may be used (e.g., heat exchangers, plant cooling water exchangers, etc). In some embodiments, the ethylene-depleted stream 7 is thermally contacted with the silane-containing feed stream 3 (e.g., after condensing) such as by thermal contact in an interchanger (not shown). For purposes of the present disclosure, the interchanger serves as both the "heater" and "cooler" as referenced above. When such an interchanger is used, additional heaters and coolers are typically used to reach the desired temperature set points for the respective streams.

The light-ends distillation column 15 may be operated at temperatures and pressures suitable for separating compounds having a boiling point less than silane from silane as appreciated by those of skill in the art. For example, the light-ends distillation column 15 may be operated at an overhead fraction 43 temperature of from about −130° C. to about −50° C. or from about −110° C. to about −80° C. and an overhead fraction pressure of from about 1100 kPa to about 2500 kPa or from about 1400 kPa to about 2200 kPa. The bottoms fraction 31 temperature may be from about −120° C. to about −30° C., from about −120° C. to about −60, or from about −60 to about −30.

Upon discharge from the light-ends distillation column 15, the silane-depleted overhead fraction 43 may be neutralized and disposed as a waste stream. In some embodiments, the overhead fraction may be processed to recover further silane as disclosed in U.S. patent application Ser. No. 13/246,571, filed Sep. 27, 2011, published as U.S. Patent Publication No. 2012/0079847.

The silane-enriched bottoms fraction 31 may be introduced into a heavy-ends distillation column 10 to produce a silane-enriched overhead fraction 13 and a silane-depleted bottoms fraction 8 relative to the silane-enriched bottoms fraction 31 produced from the light-ends distillation column 15. The silane-depleted bottoms fraction 8 is enriched in compounds having a boiling point greater than silane. As used herein, "heavy-ends distillation column" refers to a distillation column in which at least about 50 wt % to the compounds with a boiling point greater than silane are separated from the heavy-ends distillation column feed stream (or feed streams when more than one feed streams are used). Generally, these separated compounds are removed from the heavy-ends distillation column 10 in silane-depleted bottoms fraction 8. In some embodiments of the present disclosure, the bottoms fraction 8 contains at least about 50 wt % of the compounds with a boiling point greater than silane in the silane-containing stream 3 and, in other embodiments, at least about 60 wt %, at least about 75 wt %, at least about 90 wt % or even at least about 95 wt % of the compounds with a boiling point greater than silane in the silane-containing stream 3. Generally, the bottoms fraction 8 is enriched in compounds with a boiling point greater than silane including ethylsilane and ethane.

The heavy-ends distillation column 10 may be operated at temperatures and pressures suitable for separating compounds having a boiling point greater than silane from silane as appreciated by those of skill in the art. In this regard, relatively higher bottoms fraction 8 temperatures generally reduce the amount of silane in the bottoms fraction 8 but increase the amount of impurities in the silane-enriched overhead fraction 13. Accordingly, the column 10 may be operated below temperatures at which the amount of impurities in the overhead fraction 13 is unacceptable to purification operations. For example, the heavy-ends distillation column 10 may be operated at a bottoms fraction 8 temperature of less than about 10° C. and, in other embodiments, less than about 0° C., less than about −10° C., less than about −20° C., less than about −30° C. or even less than about −40° C. (e.g., from about −50° C. to about 10° C., from about −50° C. to about 0° C. or from about −40° C. to about 0° C.). The distillation column 11 may be operated at pressures from about 1250 kPa (atmospheric) to about 3000 kPa or from about 1500 kPa to about 2500 kPa.

The overhead fraction 13 contains purified silane which may be used in further processing (e.g., epitaxial deposition, thermal decomposition or product load-out before shipping). The overhead fraction 13 may contain less than about 10 ppm by weight ethylene and ethane or even less than about 1 ppm, less than about 0.1 ppm or even less than about 0.01 ppm ethylene and ethane. Upon discharge from the heavy-ends distillation column 10, the silane-depleted bottoms fraction 8 may be neutralized and disposed of as a waste stream. Alternatively, the bottoms fraction 8 may be processed to recover an amount of silane (e.g., by further distillation) as disclosed in U.S. patent application Ser. No. 12/898,494, filed Oct. 5, 2010, published as U.S. Patent Publication No. 2012/0080304.

By arranging the process such that the reactor 20 is upstream of the heavy-ends distillation column 10 rather than downstream, a separate distillation column (or multiple columns when crude silane is processed in a parallel arrangement) for removal of ethylsilane and/or ethane may be eliminated as these compounds can be removed in the heavy-ends distillation column 10. Further, by arranging the process such that reactor 20 is upstream of the light-ends distillation column 15, the amount of heat that is input into the reactor feed may be reduced (i.e., the difference in temperature between the stream discharged from the previous unit operation (e.g., crude silane) and the stream that enters the reactor is reduced). Further, the amount of heat removed (i.e., cooling) from the ethylene-depleted stream discharged from the reactor may be reduced (i.e., the difference in temperature between the stream discharged from the reactor and the stream input into the next unit operation (i.e., light-distillation column as shown in FIG. 1) may be reduced). Also, conversion of ethylene to ethylsilane and/or ethane increases the relative amount of compounds that have a boiling point greater than silane (i.e., both ethylsilane and ethane have boiling points greater than silane while ethylene has a boiling point similar to silane) in the stream introduced into the light-ends column 15 which allows the light-ends to be more easily separated from silane in the light-ends column.

In some embodiments of the present disclosure, the difference in temperature between the stream discharged from the previous unit operation (i.e., crude silane after compression) and the stream that enters the reactor 20 is less than about 125° C., less than about 100° C. or even less than about 75° C. (e.g., the difference in temperatures may range from about 25° C. to about 125° C. or from about 25° C. to about 100° C.). Alternatively or in addition, the difference in temperature between the stream discharged from the reactor 20 and the stream input into the next unit operation (i.e., light-ends distillation column as shown in FIG. 1) may be less than about 300° C. or less than about 250° C. or even less than about 225° C. (e.g., from about 150° C. to about 300° C., from about 150° C. to about 250° C. or from about 200° C. to about 250° C.).

It should be noted that while the process for purifying the silane-containing stream 3 has been described herein and illustrated in FIG. 1 with the light-ends column being upstream of the heavy-ends column, in some embodiments the order of the light-ends column and heavy-ends column is reversed. In such embodiments, the ethylene-depleted stream discharged from the reactor is introduced into the heavy-ends column to produce a silane-enriched overhead fraction and a silane-depleted bottoms fraction relative to the ethylene-depleted stream. The silane-depleted bottoms fraction is enriched in at least one of ethylsilane and ethane relative to the ethylene-depleted stream. The overhead stream produced from the heavy-ends column is introduced into the light-ends column to produce a silane-depleted overhead fraction and a silane-enriched bottoms fraction relative to the overhead fraction produced from the heavy-ends distillation column. The silane-depleted overhead fraction is enriched in compounds with a boiling point less than silane relative to the overhead fraction produced from the heavy-ends distillation column. The bottoms fraction produced from the light-ends column may be recovered as purified silane.

In this regard, the process conditions in embodiments wherein the heavy-ends distillation column is upstream of the light-ends column may be the same as those described above for embodiments wherein the light-ends distillation column is upstream of the heavy-ends distillation column.

Systems for Purifying Silane

The processes of the present disclosure may be carried out in a system for purifying silane such as, for example, the system shown in FIG. 1 and described above. In some embodiments and as shown in FIG. 1, the system purifies a silane-containing stream 3 comprising silane, ethylene and one or more compounds having a boiling point less than silane.

The system includes a reactor 20 for converting ethylene within a silane-containing stream 3 to at least one of ethylsilane and ethane and for producing an ethylene-depleted stream 7 relative to the silane-containing stream 3. The system also includes a light-ends distillation column 15 for producing a silane-depleted overhead fraction 43 and a silane-enriched bottoms fraction 31 relative to the ethylene-depleted stream 7, the silane-enriched bottoms fraction 31 comprising silane and at least one of ethylsilane and ethane. The reactor 20 may include a zeolite catalyst which may form a molecular sieve. In some embodiments the catalyst is a zeolite-supported platinum, palladium or nickel catalyst. The system also includes a conveying apparatus for conveying the ethylene-depleted stream 7 from the reactor 20 to the light-ends distillation column 15.

The system may include a heater for heating the silane-containing stream 7 prior to introduction into the reactor 20 and a conveying apparatus for conveying the silane-containing stream 3 from the heater to the reactor 20. The system may include a cooler for cooling the ethylene-depleted stream 7 prior to introduction into the light-ends distillation column 15. In embodiments in which a cooler is used, a conveying apparatus conveys the ethylene-depleted stream 7 from the reactor 20 to the cooler and a conveying apparatus conveys the ethylene-depleted stream 7 from the cooler to the light-ends distillation column 15.

The system may also include unit operations for removing compounds having a boiling point greater than silane. The system may include a heavy-ends distillation column 10 for producing a silane-enriched overhead fraction 13 and a silane-depleted bottoms fraction 8 relative to the silane-enriched bottoms fraction 31 produced from the light-ends distillation column 15. The silane-depleted bottoms fraction 8 is enriched in at least one of ethylsilane and ethane. The system includes a conveying apparatus for conveying the silane-enriched bottoms fraction 31 produced from the light-ends distillation column 15 to the heavy-ends distillation column 10.

It should be noted that while the system for purifying the silane-containing stream has been described herein and illustrated in FIG. 1 with the light-ends column being upstream of the heavy-ends column, in some systems the order of the light-ends column and heavy-ends column may be reversed. Such systems will include conveying apparatus for conveying the ethylene-depleted stream from the reactor to the heavy-ends distillation column and conveying apparatus for conveying the overhead fraction produced from the heavy-ends distillation column to the light-ends distillation column. The system may also include heaters and coolers similar to the system described above in which the light-ends column is upstream of the heavy-ends column.

In this regard, suitable conveying apparatus for use in the systems described above and shown in FIG. 1 are conventional and well known in the art. Suitable conveying apparatus for the transfer of gases include, for example, a recirculation fan or blower and transfer lines associated therewith (e.g., associated ductwork). Suitable conveying apparatus for conveying liquids include, for example, pumps and compressors and transfer lines associated therewith (e.g., associated piping). In this regard, it should be understood that use of the phrase "conveying apparatus" herein is not meant to imply direct transfer from one unit of the system to another but rather only that the material is transferred from one unit to another by any number of indirect transfer parts and/or mechanisms. For example, material from one unit may be conveyed to further processing units (e.g., purification) and then conveyed to the second unit. In this example, each unit of conveyance including the intermediate processing equipment itself may be considered to be the "conveying apparatus" and the phrase "conveying apparatus" should not be considered in a limiting sense.

Preferably, all equipment utilized in the systems for purifying silane is resistant to corrosion in an environment that includes exposure to compounds used and produced within the system. Suitable materials of construction are conventional and well-known in the field of the disclosure and include, for example, carbon steel, stainless steel, MONEL alloys, INCONEL alloys, HASTELLOY alloys, nickel, graphite (e.g., extruded or iso-molded) and silicon carbide (e.g., converted graphite or extruded).

EXAMPLES

Example 1

Figure 2:
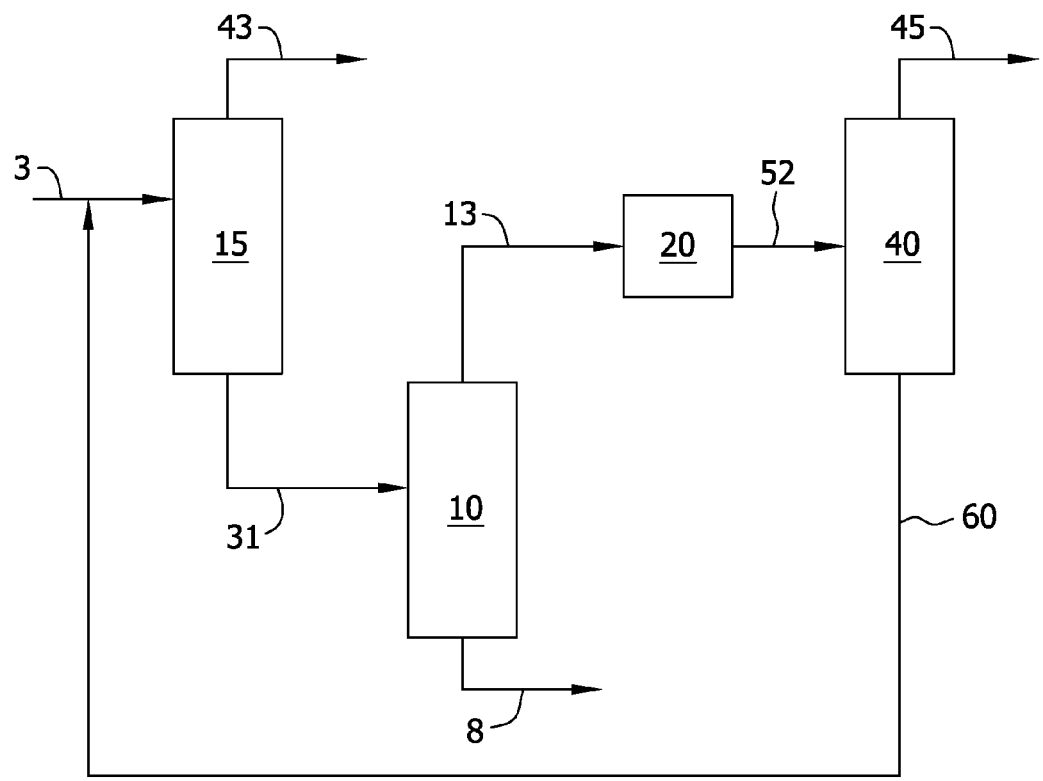
FIG. 2 is a schematic of a conventional system for purifying silane from a silane-containing stream that contains ethylene.

Modeling the Purification of Silane after Conversion of Ethylene to Ethane and/or Ethylsilane and Comparison to Conventional Purification Processes Purification of silane by use of the system shown in FIG. 1 was modeled on Aspen software. Two additional systems were modeled: (1) a system as shown in FIG. 2 in which the reactor 20 is downstream of the heavy-ends distillation column 10 and ethylsilane and ethane are removed in a third column 40 and (2) a system shown in FIG. 3 in which the reactor 20 is downstream of the light-ends column 15 and upstream 10 of the heavy-ends distillation column 10. The systems of FIGS. 1-3 were modeled with various heater/coolers and interchangers (not shown) to more accurately model plant conditions. The crude-silane stream 3 was simulated at a feed temperature of 113° C. (235° F.). The feed introduced into the light-ends column 15 was 29° C. (85° F.) and the bottoms fraction 31 was −34.4° C. (−30° F.) and the overhead fraction 43 was −90° C. (−130° F.). The light-ends column 15 was simulated at a pressure of about 2,068 kPa gauge (300 psig). The feed to the reactor 20 was at a temperature of 149° C. (300° F.). The feed to the heavy-ends column 10 was −34.4° C. (−30° F.) and the bottoms fraction 8 was at a temperature of −18° C. (0° F.) and the overhead fraction 15 was at a temperature of −38° C. (−37° F.). The heavy-ends column 10 was simulated at a pressure of 1,931 kPa gauge (280 psig). It should be understood that the operating conditions described in Example 1 are exemplary and other conditions may be used.

The silane-containing stream 3 which was treated in accordance with systems 1-3 contained the following components:

TABLE 1

Composition of Crude Silane Stream used in Simulations.

| Component | Mole Flow (mol/hr) |
|---|---|
| Silane | 38.9566 |
| Hydrogen | 1.5114 |

TABLE 1-continued

Composition of Crude Silane Stream used in Simulations.

| Component | Mole Flow (mol/hr) |
|---|---|
| Ethylene | 0.0014 |
| Ethane | 0.1635 |
| Ethylsilane | 0.2870 |
| Diethylsilane | 0.0040 |
| Nitrogen | 0.2311 |
| Methane | 0.0100 |

The composition of the purified silane stream (designated as "13" in FIGS. 1 and 3 and "45" in FIG. 2) for the three modeled systems is shown in Table 2 below

TABLE 2

Composition of Purified Silane in Simulations ("nd"—none detected).

Figure 3:
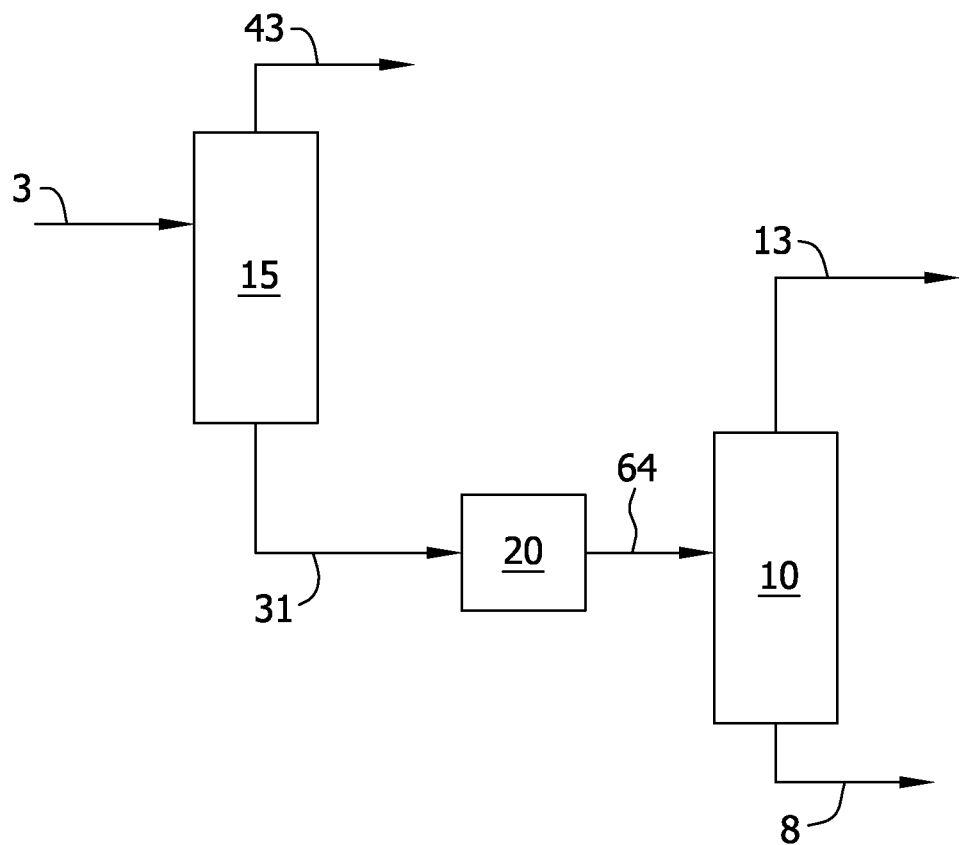
FIG. 3 is a schematic of another conventional system for purifying silane from a silane-containing stream that contains ethylene.

| Component | FIG. 1 Flow Arrangement (mol/hr) | FIG. 2 Flow Arrangement (mol/hr) | FIG. 3 Flow Arrangement (mol/hr) |
|---|---|---|---|
| Silane | 37.581 | 37.549 | 37.581 |
| Hydrogen | nd | nd | nd |
| Ethylene | $1.25 \times 10^{-6}$ | $1.24 \times 10^{-6}$ | $1.23 \times 10^{-6}$ |
| Ethane | $2.3 \times 10^{-7}$ | $2.2 \times 10^{-7}$ | $2.7 \times 10^{-7}$ |
| Ethylsilane | nd | nd | nd |
| Diethylsilane | nd | nd | nd |
| Nitrogen | nd | nd | nd |
| Methane | $5.21 \times 10^{-6}$ | $5.21 \times 10^{-6}$ | $5.21 \times 10^{-6}$ |

As can be seen from Table 2, silane product purity was nearly the same for all three simulations. The flow arrangement of the present disclosure shown in FIG. 1 is able to achieve such a purity with a simpler design and arrangement (e.g., less exchangers and/or less exchanger surface area) relative to the convention processes of FIGS. 2 and 3.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A process for purifying a silane-containing stream, the stream comprising silane, ethylene and one or more compounds with a boiling point less than silane, the process comprising:
    introducing the silane-containing stream into a reactor to convert ethylene to at least one of ethylsilane and ethane and to produce an ethylene-depleted stream relative to the silane-containing stream; and
    introducing the ethylene-depleted stream into a heavy-ends distillation column to produce a silane-enriched overhead fraction and a silane-depleted bottoms fraction relative to the ethylene-depleted stream, the silane-depleted bottoms fraction being enriched in at least one of ethylsilane and ethane relative to the ethylene-depleted stream; and
    introducing the overhead fraction produced from the heavy-ends distillation column into a light-ends distillation column to produce a silane-depleted overhead fraction and a silane-enriched bottoms fraction relative to the overhead fraction produced from the heavy-ends distillation column, the silane-depleted overhead fraction being enriched in compounds with a boiling point less than silane relative to the overhead fraction produced from the heavy-ends distillation column.

2. The process as set forth in claim 1 wherein the silane-containing stream comprises compounds having a boiling point greater than silane other than ethylsilane and ethane, wherein the silane-depleted bottoms fraction produced from the heavy-ends distillation column is enriched in such compounds.

3. The process as set forth in claim 2 wherein the one or more compounds having a boiling point greater than silane are selected from the group consisting of diethyl silane, toluene, dimethoxyethane and mixtures thereof.

4. The process as set forth in claim 1 wherein the silane-containing stream is heated to a temperature of at least about 100° C. prior to entry into the reactor.

5. The process as set forth in claim 1 wherein the silane-containing stream is pressurized to a pressure of at least about 2200 kPa prior to introduction into the reactor.

6. The process as set forth in claim 1 wherein the silane-containing stream is contacted with a zeolite catalyst in the reactor.

7. The process as set forth in claim 6 wherein the reactor comprises a zeolite catalyst in the form of a molecular sieve.

8. The process as set forth in claim 1 wherein the reactor comprises a zeolite-supported platinum, palladium or nickel catalyst.

9. The process as set forth in claim 1 wherein the one or more compounds having a boiling point less than silane are selected from the group consisting of hydrogen, nitrogen, and methane.

10. The process as set forth in claim 1 wherein at least about 75% of the ethylene introduced into the reactor in the silane-containing stream is converted to at least one of ethylsilane and ethane.

* * * * *